(12) United States Patent
Alsop et al.

(10) Patent No.: US 11,366,186 B2
(45) Date of Patent: Jun. 21, 2022

(54) SYSTEM AND METHOD FOR MICROFLUIDIC PARAHYDROGEN INDUCED POLARIZATION HYPERPOLARIZER FOR MAGNETIC RESONANCE IMAGING (MRI) AND NUCLEAR MAGNETIC RESONANCE (NMR) APPLICATIONS

(71) Applicant: Beth Israel Deaconess Medical Center, Inc., Boston, MA (US)

(72) Inventors: David Alsop, Newton, MA (US); Aaron Grant, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 342 days.

(21) Appl. No.: 16/323,596

(22) PCT Filed: Aug. 9, 2017

(86) PCT No.: PCT/US2017/046054
§ 371 (c)(1),
(2) Date: Feb. 6, 2019

(87) PCT Pub. No.: WO2018/031629
PCT Pub. Date: Feb. 15, 2018

(65) Prior Publication Data
US 2019/0204397 A1    Jul. 4, 2019

Related U.S. Application Data

(60) Provisional application No. 62/372,554, filed on Aug. 9, 2016.

(51) Int. Cl.
*G01R 33/28*    (2006.01)
*A61K 49/08*    (2006.01)
(Continued)

(52) U.S. Cl.
CPC ............ *G01R 33/282* (2013.01); *A61K 49/08* (2013.01); *A61K 49/10* (2013.01); *G01R 33/302* (2013.01); *G01R 33/5605* (2013.01)

(58) Field of Classification Search
CPC ........ A61K 49/08; A61K 49/10; A61K 49/06; G01R 33/282; G01R 33/302; G01R 33/5605; G01R 33/5601
See application file for complete search history.

(56) References Cited

U.S. PATENT DOCUMENTS 6,574,495 B1 *  6/2003  Golman ................. A61K 49/06
                                                600/420
8,071,035 B2    12/2011  Elizarov
(Continued)

FOREIGN PATENT DOCUMENTS

WO      2014/150944      9/2014

OTHER PUBLICATIONS

L. S. Bouchard, S. R. Burt, M. S. Anwar, K. V. Kovtunov, I. V. Koptyug, A. Pines, NMR imaging of catalytic hydrogenation in microreactors with the use of parahydrogen. Science 319, 442 (2008) (Year: 2008).*

(Continued)

*Primary Examiner* — Steven L Yeninas
(74) *Attorney, Agent, or Firm* — Quades & Brady LLP (57) ABSTRACT

Systems and methods are provided for producing hyperpolarized materials for use during a magnetic resonance imaging (MRI) or nuclear magnetic resonance (NMR) process. The system and methods include the use of microfluidic and/or microreactor methods in one or more of the stages of parahydrogen production, enriched substrate production, and spin order transfer from the parahydrogen to a substrate.

32 Claims, 6 Drawing Sheets

(51) Int. Cl.
   A61K 49/10    (2006.01)
   G01R 33/30    (2006.01)
   G01R 33/56    (2006.01)

(56) References Cited

U.S. PATENT DOCUMENTS

| | | | |
|---|---|---|---|
| 9,261,295 B1* | 2/2016 | Schmidt | F25D 16/00 |
| 2003/0194369 A1* | 10/2003 | Prasad | B01J 8/009 |
| | | | 423/658.2 |
| 2004/0024307 A1* | 2/2004 | Golman | A61K 49/18 |
| | | | 600/420 |
| 2006/0127313 A1* | 6/2006 | Goldman | G01R 33/282 |
| | | | 424/9.3 |
| 2006/0127314 A1* | 6/2006 | Ardenkjaer-Larsen | |
| | | | A61P 43/00 |
| | | | 424/9.3 |
| 2007/0148054 A1* | 6/2007 | Takahashi | B01J 19/0093 |
| | | | 422/130 |
| 2008/0003138 A1* | 1/2008 | Sakurai | B01L 3/502707 |
| | | | 422/68.1 |
| 2010/0219826 A1* | 9/2010 | Duckett | A61K 49/06 |
| | | | 324/307 |
| 2011/0095759 A1* | 4/2011 | Bhattacharya | G01R 33/48 |
| | | | 324/307 |
| 2012/0176130 A1* | 7/2012 | Ledbetter | G01R 33/26 |
| | | | 324/301 |
| 2013/0267036 A1 | 10/2013 | Tang et al. | |
| 2014/0034481 A1* | 2/2014 | Waddell | G01R 33/282 |
| | | | 204/157.15 |
| 2014/0079641 A1 | 3/2014 | Alsop | |
| 2014/0112870 A1* | 4/2014 | Waddell | A61K 49/06 |
| | | | 424/9.3 |
| 2014/0125334 A1 | 5/2014 | Owers-Bradley et al. | |
| 2014/0132265 A1* | 5/2014 | Waddell | G01R 33/543 |
| | | | 324/310 |
| 2014/0223923 A1* | 8/2014 | Kalechofsky | A61K 49/10 |
| | | | 62/3.1 |
| 2014/0376794 A1 | 12/2014 | Dumoulin et al. | |
| 2015/0022204 A1* | 1/2015 | Bhattacharya | G01R 33/282 |
| | | | 324/309 |
| 2015/0133341 A1* | 5/2015 | Lerche | G01N 33/5005 |
| | | | 506/10 |
| 2015/0217262 A1* | 8/2015 | Wagner | G01R 33/282 |
| | | | 424/9.3 |
| 2015/0323616 A1* | 11/2015 | Tang | G01R 33/282 |
| | | | 324/309 |
| 2016/0169998 A1* | 6/2016 | Warren | G01R 33/445 |
| | | | 324/309 |
| 2016/0252532 A1* | 9/2016 | Schilling | A61B 5/055 |
| | | | 424/9.3 |
| 2017/0008763 A1* | 1/2017 | Karng | B01D 53/24 |
| 2017/0153218 A1* | 6/2017 | Chekmenev | G01N 33/287 |

OTHER PUBLICATIONS

Hovener, J-B. et al. 2012. Safety, concept, experimental design and quality assurance for parahydrogen in a clinical setting. Proc. Int. Soc. Mag. Reson. Med. May 5, 2012. p. 1674.

Zhivonitko, V. V., et al. "Characterization of microfluidic gas reactors using remote-detection MRI and parahydrogen-induced polarization." Angewandte Chemie (International ed. in English) 51.32 (2012): 8054.

Dechent, J. F., et al. "Continuous Proton Hyperpolarization via SABRE and Hollow Fibre Membranes." Proc. Int. Soc. Mag. Reson. Med. Apr. 7, 2013. p. 1937.

Elvira, K. S., et al. "The past, present and potential for microfluidic reactor technology in chemical synthesis." Nature Chemistry, vol. 5, No. 11, 2013. pp. 905-915.

Feng, B, et al. "A pulsed injection parahydrogen generator and techniques for quantifying enrichment." Journal of Magnetic Resonance 214 (2012): 258-262.

European Patent Office, Extended European Search Report for application 17840190.7 dated Mar. 12, 2020. 7 pages.

International Search Report and Written Opinion for International Patent Application No. PCT/US2017/046054 dated Nov. 30, 2017.

Adamo, A. et al. On-demand continuous-flow production of pharmaceuticals in a compact, reconfigurable system. Science 352 (6281):61-7. (2016.

Adams, R.W., et al., Reversible Interactions with para-Hydrogen Enhance NMR Sensitivity by Polarization Transfer. Science, 2009. 323(5922): p. 1708-1711.

Albers, M.J., et al., Hyperpolarized 13C lactate, pyruvate, and alanine: noninvasive biomarkers for prostate cancer detection and grading. Cancer Res, 2008. 68(20): p. 8607-15.

Ardenkjaer-Larsen, J.H., et al., Increase in signal-to-noise ratio of >10000 times in liquid-state NMR. Proceedings of the National Academy of Sciences of the United States of America, 2003. 100(18): p. 10158-10163.

Bergbreiter DE, et al. Polyisobutylene-supported phosphines as recyclable and regenerable catalysts and reagents. J Org Chem. 2011;76(16):6912-7. Epub Jul. 1, 2011. doi: 10.1021/jo201097x. PubMed PMID: 21714575.

Bouchard, L.S., et al., NMR imaging of catalytic hydrogenation in microreactors with the use of para-hydrogen. Science, 2008. 319(5862): p. 442-445.

Bowers CR, et al. Transformation of symmetrization order to nuclear-spin magnetization by chemical reaction and nuclear magnetic resonance. Physical Review Letters. 1986;24:2645-8.

Bowers, C.R. et al, Parahydrogen and synthesis allow dramatically enhanced nuclear alignment. Journal of the American Chemical Society, 1987. 109: p. 5541-5542.

Cao, H.S., et al., Micromachined cryogenic cooler for cooling electronic devices down to 30 K. Journal of Micromechanics and Microengineering, 2013. 23(2): p. 6.

Cavallari, E., et al., The (13)C hyperpolarized pyruvate generated by ParaHydrogen detects the response of the heart to altered metabolism in real time. Sci Rep, 2018. 8(1): p. 8366.

Coffey AM, et al. Open-Source Automated Parahydrogen Hyperpolarizer for Molecular Imaging Using C-13 Metabolic Contrast Agents. Anal Chem. 2016;88(16):8279-88. doi: 10.1021/acs.analchem. 6b02130. PubMed PMID: WOS:000381654800055.

Cunningham, C.H., et al., Hyperpolarized 13C Metabolic MRI of the Human Heart: Initial Experience. Circ Res, 2016. 119(11): p. 1177-1182.

Day, S.E., et al., Detecting tumor response to treatment using hyperpolarized 13C magnetic resonance imaging and spectroscopy. Nature Medicine, 2007. 13(11): p. 1382-1387.

Devience SJ, et al. Metabolic imaging of energy metabolism in traumatic brain injury using hyperpolarized [1-13C] pyruvate. Sci Rep. 2017;7(1):1907. Epub May 17, 2017. doi: 10.1038/s41598-017-01736-x. PubMed PMID: 28507314; PMCID: PMC5432492.

Gallagher, F.A., et al., Magnetic resonance imaging of pH in vivo using hyperpolarized 13C-labelled bicarbonate. Nature, 2008. 453(7197): p. 940-3.

Goldman M, et al. Conversion of a proton pair para order into C-13 polarization by rf irradiation, for use in MRI. Comptes Rendus Physique. 2005;6(4-5):575-81. PubMed PMID: ISI:000232099400013.

Golman, K., et al., Cardiac metabolism measured noninvasively by hyperpolarized 13C MRI. Magn Reson Med, 2008. 59(5): p. 1005-13.

Golman, K., et al., Parahydrogen-Induced Polarization in Imaging: Subsecond 13C Angiography. Magnetic Resonance in Medicine, 2001. 46: p. 1-5.

Grant, A.K., et al., Perfusion imaging with a freely diffusible hyperpolarized contrast agent. Magn Reson Med, 2011. 66(3): p. 746-55.

Herrmann WA, et al. Syntheses of Water-Soluble Phosphines and their Transition Metal Complexes. Inorganic Syntheses: John Wiley & Sons, Inc.; 1998. p. 8-25.

Hovener JB, et al. Quality assurance of Pasadena hyperpolarization for 13C biomolecules. MAGMA. 2009;22(2):123-34. doi: 10.1007/s10334-008-0154-y. PubMed PMID: 19067009; PMCID: 2664864.

(56) References Cited

OTHER PUBLICATIONS

Hovener, J.B., et al., A continuous-flow, high-throughput, high-pressure para hydrogen converter for hnyperpolarization in a clinical setting. Nmr in Biomedicine, 2013. 26(2): p. 124-131.

Hu H, et al. Phosphoinositide 3-Kinase Regulates Glycolysis through Mobilization of Aldolase from the Actin Cytoskeleton. Cell. 2016;164(3):433-46. doi: 10.1016/j.cell.2015.12.042. PubMed PMID: 26824656.

Johannesson H, et al. Transfer of para-hydrogen spin order into polarization by diabatic field cycling. Comptes Rendus Physique. 2004;5:314-24.

Koellisch, U., et al., Investigation of metabolic changes in STZ-induced diabetic rats with hyperpolarized [1-13C] acetate. Physiol Rep, 2015. 3(8).

Laustsen, C., et al., Assessment of early diabetic renal changes with hyperpolarized [1-(13) C]pyruvate. Diabetes Metab Res Rev, 2013. 29(2): p. 125-9.

Leadbeater NE, et al. Preparation of polymer-supported ligands and metal complexes for use in catalysis. Chem Rev. 2002;102(10):3217-73. Epub Oct. 10, 2002, PubMed PMID: 12371884.

Luo, J., et al. "Rhodium-Catalyzed Selective Partial Hydrogenation of Alkynes." Organometallics 34.12 (2015): 3021-3028.

Mackenzie, J.D., et al., Detection of inflammatory arthritis by using hyperpolarized 13C-pyruvate with MR imaging and spectroscopy. Radiology, 2011. 259(2): p. 414-20.

Malloy, C.R., et al, Could 13C MRI assist clinical decision-making for patients with heart disease? NMR Biomed, 2011. 24(8): p. 973-9.

Melson, SJ et al. Metabolic imaging of patients with prostate cancer using hyperpolarized [1-$^{13}$C]pyruvate. Sci Transl Med. Aug. 14, 2013;5(198):198ra108.

Olsson LE, et al. MR Coronary Angiography in Pigs with Intraarterial Injection of a Hyperpolarized C13 Substance. Magn Reson Med. 2006;55:731-7.

Pagliaro, T., et al., Toward Dynamic 3D Cardiac Perfusion Imaging Using bSSFP and Hyperpolarized tert-Butanol. Proceedings of the 25th Meeting of the International Society for Magnetic Resonance in Medicine, 2017: p. 558.

Pascali G, et al. Microfluidics in radiopharmaceutical chemistry. Nucl Med Biol. 2013;40(6):776-87. doi: 10.1016/j.nucmedbio.2013.04.004. PubMed PMID: 23684316.

Pravica MG, et al. Net NMR alignment by adiabatic transport of parahydrogen addition products to high magnetic field. Chemical Physics Letters. 1987;145(4):255-8.

Pullinger, B., et al., Metabolism of hyperpolarized [1-(1)(3)C]pyruvate in the isolated perfused rat lung—an ischemia study. NMR Biomed, 2012. 25(10): p. 1113-8.

Reineri, F., et al, ParaHydrogen Induced Polarization of 13C carboxylate resonance in acetate and pyruvate. Nat Commun, 2015. 6: p. 5858.

Salnikov, OG et al., Production of Catalyst-Free Hyperpolarised Ethanol Aqueous Solution via Heterogeneous Hydrogenation with Parahydrogen. Sci Rep. 2015; 5: 13930.

Schrock, R.R. et al, "Catalytic hydrogenation using cationic rhodium complexes. I. Evolution of the catalytic system and the hydrogenation of olefins." Journal of the American Chemical Society 98.8 (1976): 2134-2143.

Todd, D.J. et al, Gadolinium-Induced Fibrosis. Annu Rev Med, 2016. 67: p. 273-91.

Tyler, D.J., Cardiovascular Applications of Hyperpolarized MRI. Curr Cardiovasc Imaging Rep, 2011.4(2): p. 108-115.

Vinogradov, E. et al, Hyperpolarized long-lived states in solution NMR: three-spin case study in low field. J Magn Reson, 2008. 194(1): p. 46-57.

Weitzel, D.H., et al., Ortho-Para Catalysis in Liquid-Hydrogen Production. Journal of Research of the National Bureau of Standards, 1958. 60(3): p. 221-227.

Witney, T.H. et al, Imaging tumour cell metabolism using hyperpolarized 13C magnetic resonance spectroscopy. Biochem Soc Trans, 2010. 38(5): p. 1220-4.

Wolber J, et al. Generating highly polarized nuclear spins in solution using dynamic nuclear polarization. Nuclear Instruments & Methods in Physics Research, Section A: Accelerators, Spectrometers, Detectors, and Associated Equipment. 2004;526:173-81.

Zhu, L., et al., An on-demand microfluidic hydrogen generator with self-regulated gas generation and self-circulated reactant exchange with a rechargeable reservoir. Microfluidics and Nanofluidics, 2011. 11(5): p. 569-578.

* cited by examiner

SYSTEM AND METHOD FOR MICROFLUIDIC PARAHYDROGEN INDUCED POLARIZATION HYPERPOLARIZER FOR MAGNETIC RESONANCE IMAGING (MRI) AND NUCLEAR MAGNETIC RESONANCE (NMR) APPLICATIONS

CROSS-REFERENCE TO RELATED APPLICATIONS

This application is a national phase of pending PCT International Application No. PCT/US2017/046054 filed Aug. 9, 2017 and claims the benefit of U.S. Provisional Patent Application Ser. No. 62/372,554, filed on Aug. 9, 2016, and entitled "SYSTEM AND METHOD FOR MICORFLUIDIC PARAHYDROGEN INDUCED POLARIZATION HYPERPOLARIZER FOR MAGNETIC RESONANCE IMAGING (MM) AND NUCLEAR MAGNETIC RESONANCE (NMR) APPLICATIONS." Each application is incorporated by reference herein as if set forth in its entirety.

FIELD

The present disclosure relates to systems and methods for creating materials for magnetic resonance imaging (MRI) or nuclear magnetic resonance (NMR) methods and systems. More particularly, the disclosure relates to a system and method for hyperpolarized magnetic resonance agents using microfluidic and microreactor technologies.

BACKGROUND

When a substance such as human tissue is subjected to a uniform magnetic field (polarizing field Bo), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Molecular imaging includes a variety of imaging modalities and employs techniques that detect molecular events such as cell signaling, gene expression, and pathologic biomarkers. These techniques seek to achieve early detection of diseases, better management of therapy treatment, and improved monitoring of cancer recurrence. MRI and NMR provide specific advantages for molecular imaging applications, due to its noninvasive nature. Traditional molecular MRI and NMR techniques rely on the administration of a contrast agent to a designated location within a subject. Oftentimes, a site-specific contrast agent is employed that interacts with a given molecule of interest. These conventional techniques, however, exhibit poor sensitivity, making the detection of the contrast agents difficult. This is especially true when imaging the brain, which has a natural barrier to exogenous chemicals.

Hyperpolarization is the nuclear spin polarization of a material far beyond thermal equilibrium conditions, which may be applied to gases such as $^{129}Xe$ and $^{3}He$, and small molecules where the polarization levels can be enhanced by a factor of $10^4$-$10^5$ above thermal equilibrium levels. Hyperpolarized noble gases are typically used in MRI of the lungs. Hyperpolarized small molecules are typically used for in-vivo metabolic imaging. For example, a hyperpolarized metabolite can be injected into animals or patients and the metabolic conversion can be tracked in real-time.

Hyperpolarization of long-lived nuclei including $^{13}C$ and $^{15}N$ offers the intriguing possibility to develop tracers for diagnostic MRI with superior properties to existing Lanthanide based relaxation agents. Unlike lanthanide agents such as Gd-DTPA where the toxic relaxation agent must be wrapped in a large protective chelate that limits it properties, $^{13}C$ and $^{15}N$ labeling can be performed on a wide range of organic chemicals appropriate for probing blood flow, permeability, molecular transport, and metabolism. These agents have the added advantage of almost zero background signal in the body and the potential to detect chemical conversion by chemical shift, or frequency, measurement. This ability to observe chemical conversion is absent in nuclear medicine studies.

Despite the promise of hyperpolarized MR agents, progress in translation has been slow. Part of the problem is the need for local production of the transiently hyperpolarized tracer. The technology involves low temperatures, catalysts or free radical agents, and then ultimately a time limited injection. One of the available technologies is called Dynamic Nuclear Polarization (DNP) hyperpolarization. DNP systems have been used to provide hyperpolarized pyruvate for initial human trials. DNP has the advantage of chemical simplicity but the technique involves very low temperatures and a very strong magnet that make it a poor candidate for miniaturization, cost reduction, and widespread use. First in human results have been demonstrated with this technology, however, and excitement is sufficient that numerous top academic institutions have installed or will soon install systems.

Therefore, hyperpolarization continues to develop as an important technique to increase contrast in MRI. It would be desirable to have systems and methods that are efficient, safe, and inexpensive to produce hyperpolarized contrast agents for MRI.

SUMMARY

The present disclosure overcomes the aforementioned drawbacks by providing a flexible, efficient, and ultimately low-cost PHIP hyperpolarized tracer production system using principles of microfluidics and microreactors.

In accordance with one aspect of the disclosure, a system is disclosed that includes a parahydrogen production system, which includes a microreactor that processes hydrogen into parahydrogen based on a request from a magnetic resonance imaging (MRI) or nuclear magnetic resonance (NMR) system. The system further includes a hyperpolarization and conversion system including a spin transfer device that receives the processed hydrogen from the microreactor and transfers spin order from the processed hydrogen to a substrate.

In accordance with another aspect of the disclosure, a method for producing polarized hydrogen is disclosed that includes at least the following steps. First, a micro hydrogen generator in a polarization delivery system generates hydrogen. A microreactor in the polarization delivery system processes the hydrogen into parahydrogen based on the request. A spin transfer device receives processed hydrogen from the microreactor. The spin transfer device transfers spin order from the processed hydrogen to a substrate.

In accordance with yet another aspect of the disclosure, a method for producing contrast agent for a magnetic resonance imaging (MRI) process is disclosed that includes using a polarization delivery system. First, a request is generated based on a subject to be scanned in the MRI system. A micro hydrogen generator in the polarization delivery system then generates hydrogen based on the request. A microreactor in the polarization delivery system processes the hydrogen into parahydrogen based on the request. A spin transfer device receives processed hydrogen from the microreactor. The spin transfer device transfers spin order from the processed hydrogen to produce the contrast agent to be injected to the subject.

In accordance with still another aspect of the disclosure, an imaging system is provided that includes a magnetic resonance imaging (MRI) or nuclear magnetic resonance (NMR) system configured to perform an MRI or NMR process to acquire imaging data from a subject to be scanned in the MRI or NMR system during the MRI or NMR process. The imaging system also includes a hyperpolarization system comprising a spin transfer device that receives hydrogen and transfers spin order from the hydrogen to a substrate and a computer system. The computer system is configured to develop a pulse sequence to carry out the MRI or NMR process generate a request for processed hydrogen to be received from the hyperpolarization system to carry out the MRI or NMR process, carry out the MRI or NMR process using the pulse sequence to acquire the imaging data from the subject having received the processed hydrogen, and reconstruct an image of the subject using the imaging data.

In accordance with another aspect of the disclosure, a microfluidic or microreactor polarization delivery system is provided. The system includes a parahydrogen production system comprising a microfluidic or microreactor that processes hydrogen based on a request from a magnetic resonance imaging (MRI) or nuclear magnetic resonance (NMR) system. The system also includes a hyperpolarization and conversion system comprising a spin transfer device that receives the processed hydrogen from the microfluidic or microreactor and transfers spin order from the processed hydrogen to a substrate.

In accordance with yet another aspect of the disclosure, a method for parahydrogen production for imaging is disclosed that includes processing hydrogen using a microfluidic or microreactor based on a request from a magnetic resonance imaging (MRI) or nuclear magnetic resonance (NMR) system and receiving the processed hydrogen from the microfluidic or microreactor and transferring spin order from the processed hydrogen to a substrate.

The foregoing and other advantages of the disclosure will appear from the following description.

DETAILED DESCRIPTION

Figure 1:
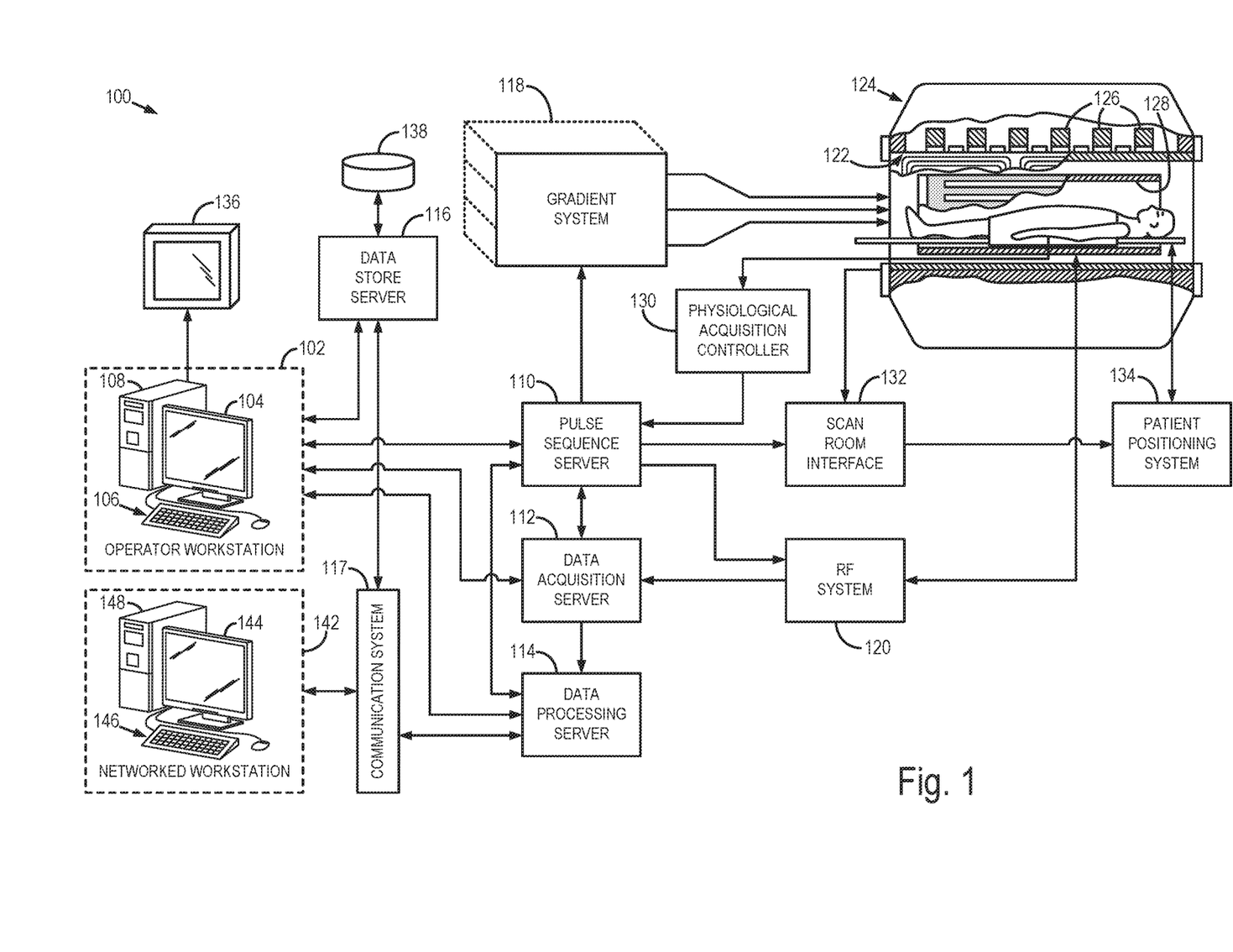
FIG. 1 is a block diagram of an MRI system which employs the present disclosure.

Referring particularly now to FIG. 1, an example of a magnetic resonance imaging (MRI) system 100 is illustrated. Though an MRI system is illustrated, one of skill will readily appreciate that the systems and methods of the present disclosure are likewise applicable to or nuclear magnetic resonance (NMR), magnetic resonance spectroscopy (MRS), and the like. Thus, as used herein, "MRI" should not be understood to be limited to imaging applications and can be more generally understood to include other resonance-based investigative techniques, including NMR, MRS, and the like.

The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2}$$ Eqn. 1;

and the phase of the received magnetic resonance signal may also be determined according to the following relationship:

$$\varphi = \tan^{-1}\left(\frac{Q}{I}\right).$$ Eqn. 2

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than passing the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchange between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
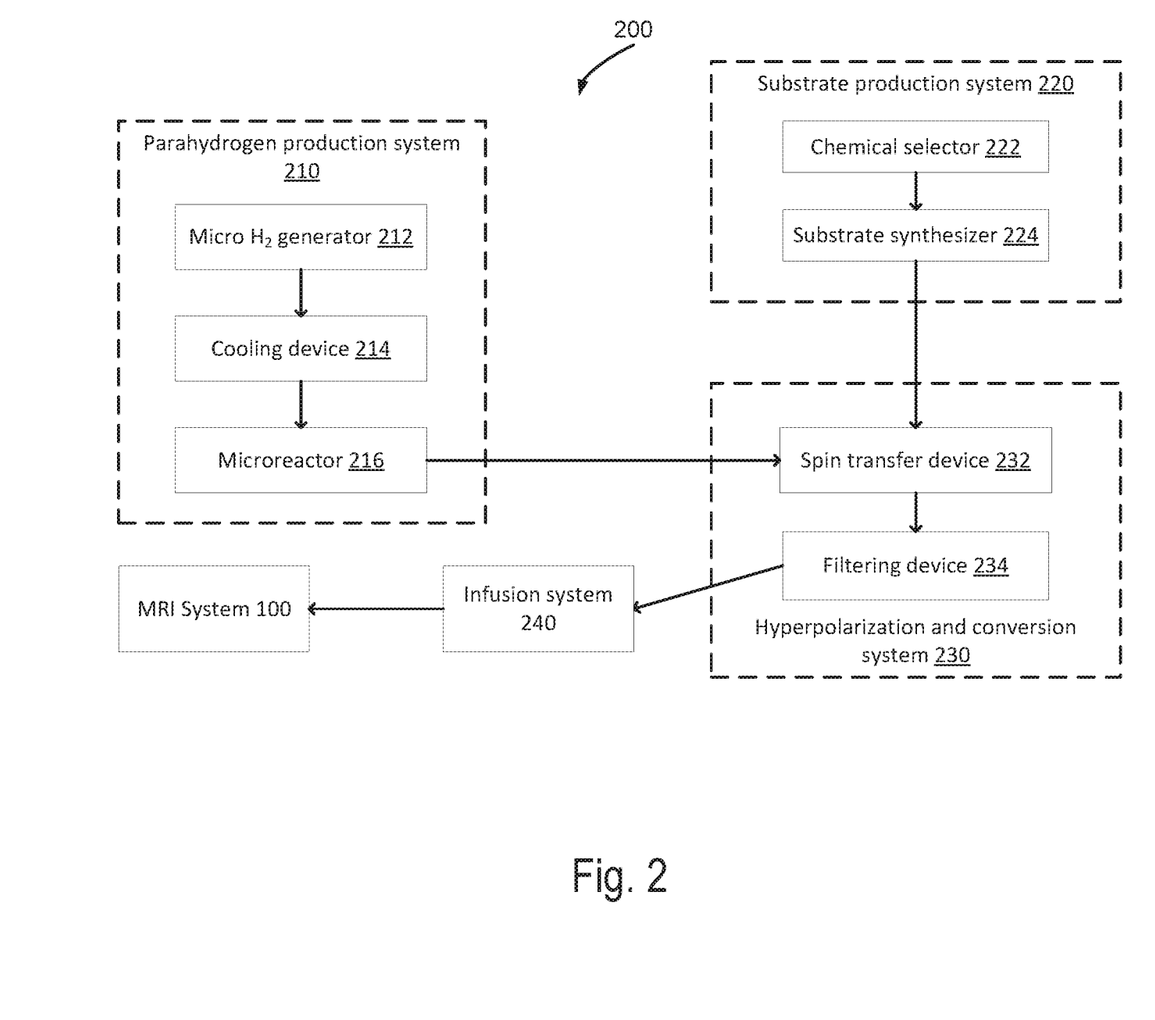
FIG. 2 is a block diagram illustrating an example polarization delivery system.

FIG. 2 is a block diagram illustrating an example polarization delivery system 200. The system 200 is a flexible and efficient system that produces tracers using principles of microfluidics and microreactors. For example, the system 200 may be based on continuous flow microfluidic methods, which have revolutionized chemical synthesis and typically provide superior consistency, simplicity, efficiency, and purity to batch synthesis methods. Such methods are particularly suitable to synthesis where high pressures, large surface areas, extreme temperatures or potentially dangerous ingredients are necessary. Since PHIP hyperpolarization may involve small quantities of potentially explosive hydrogen gas, require temperatures less than 50K if parahydrogen is produced locally, and can benefit from high pressure and large surface areas for the spin transfer or hydrogenation process, the use of microfluidic and microreactor methods may be very beneficial. Here, the hydrogen is put in a high spin order, parahydrogen state. However, it actually has zero net magnetization (or polarization).

In FIG. 2, the polarization delivery system 200 includes a parahydrogen production system 210 that produces parahydrogen. The polarization delivery system 200 further includes a substrate production system 220 that produces substrates. Both the parahydrogen production system 210 and the substrate production system 220 send output to the hyperpolarization and conversion system 230, which transfers spin order to the tracer. The whole polarization delivery system 200 may be a mobile system that can be easily controlled and moved by professionals in hospitals. The polarization delivery system 200 may also include an injector or infusion system 240, such that it infuses tracers into a subject in a MRI system 100 (or nuclear magnetic resonance (NMR)). Note that the polarization delivery system 200 need not include the parahydrogen production system 210 and the substrate production system 220 locally in one or more embodiments especially when the two systems 210 and 220 are very bulky. However, the polarization delivery system 200 can produce parahydrogen locally based on one or more requests, for example, from an MRI or nuclear magnetic resonance (NMR) that may be connected thereto and produce substrates to carry the parahydrogen for the specific subject when the two systems 210 and 220 are locally connected to the conversion system 230.

The parahydrogen production system 210 may work at temperatures below 50K so that the produced parahydrogen becomes the thermodynamically preferred state. After heating, the gas only very slowly loses its para state depending on the presence of oxygen and other trace molecules. Remote production of parahydrogen may be possible since its lifetime may be at least several weeks in an appropriately clean pressurized tank. However, local production has the benefits of simpler operation, elimination of the potentially dangerous pressurized $H_2$ tank, and control over purity and medical production standards.

As shown in FIG. 2, the parahydrogen production system 210 may include a micro $H_2$ generator 212, a cooling device 214, and a microreactor 216. For example, the micro $H_2$ generator 212 may produce parahydrogen locally based on a request, as a non-limiting example, from a connected MRI or nuclear magnetic resonance (NMR) system. The micro $H_2$ generator 212 may use any available methods for $H_2$ production. The micro $H_2$ generator 212 may produce continuous flow of $H_2$ gas meeting safety and medical grade purity controls. A method suitable for production at higher pressures may be desirable to support the subsequent cooling stage. Alternatively or additionally, the micro $H_2$ generator 212 may include a micropump to increase the pressure as well.

Conversion to parahydrogen requires cooling of the $H_2$ gas to low temperature in the range of 20K to 80K. Preferably, the temperature may need to be in the range of 20K to 40K. A cooling device 214 may be used to cool the $H_2$ gas. The cooling device 214 may achieve cooling through Joule-Thompson expansion cooling. For example, the cooling device 214 may include a two-stage cooling system such as a Joule-Thompson system using $H_2$ as the second stage coolant. Thus, the cooling device 214 directly produces cooled $H_2$ gas. Alternatively or additionally, external cooling methods for low temperature cooling may be used. Cooling the $H_2$ gas may be achieved using intermittent or micro continuous flow cooling technologies.

After the $H_2$ gas is cooled by the cooling device 214, hydrogen gas may be converted to parahydrogen in a microreactor 216. The microreactor 216 may greatly accelerate the conversion using high surface area catalysts. In one non-limiting example, the catalyst may comprise activated charcoal or Iron(III) oxide. This microreactor 216 exposes the $H_2$ gas to an appropriate catalyst on the sides or within channels through which the $H_2$ flows. After conversion, a warming stage may be used to make the $H_2$ gas reach a preset temperature for subsequent reactions. The preset temperature may be determined by the optimal temperature of the reaction, engineering considerations such as material tolerance and condensation, and the temperature desired for introduction in the MRI or NMR. For example, body temperature (310K) may be desirable for introduction in human studies.

Hyperpolarized MR relies on long relaxation time nuclei such as $^{13}C$. The $^{13}C$ nuclei are not present in high abundance in nature. Thus, enriched version of the $^{13}C$ substrate need to be produced. While enriched substrates may be produced off-site, local production has some advantages. Thus, the polarization delivery system 200 further includes a substrate production system 220 for local production of substrates.

The substrate production system 220 may include a chemical selector 222 to select medical grade $^{13}C$ or $^{15}N$ enriched molecules for use as input chemicals for the substrate production system 220. In some aspects, the input chemicals may include enriched versions of $CO_2$ or simple organic molecules. The input chemicals may be transferred from the chemical selector 222 to a substrate synthesizer 224, which converts input chemicals to the substrate. For example, the synthesizer 224 may synthesize more complex substrates from the input chemicals with a reduced cost. The substrate synthesizer 224 may help to control chemical purity, and enable flexible production of different hyperpolarized agents if needed. The substrate synthesizer 224 may use different synthesis methods depending on the desired hyperpolarized agent. The substrate synthesizer 224 provides a flexible system for local production of specific chemicals using microfluidic methods.

As shown in FIG. 2, the polarization delivery system 200 further includes a hyperpolarization and conversion system 230. The hyperpolarization and conversion system 230 includes a spin transfer device 232 and a filtering device 234. For example, the hyperpolarization and conversion system 230 may include a spin transfer device 232 that receives parahydrogen from the parahydrogen production system 210 and substrate from the substrate production system 220.

The hyperpolarization and conversion system 230 is fundamental to PHIP and its improvement with microfluidic and microreactor methods. In the hyperpolarization and conversion system 230, spin order transfer may be performed using continuous flow inputs from systems 210 and 220. Since the products from systems 210 and 220 are not particularly short-lived, another embodiment of the present disclosure includes storing accumulating products from systems 210 and 220 for input into a more rapid and higher volume conversion system 230.

The spin transfer device 232 may increase the pressure of the parahydrogen with a miniature pump to increase efficiency of the spin transfer or hydrogenation reaction. The spin transfer device 232 may use a plurality of strategies for spin order transfer.

There are several examples for spin order transfer. Parahydrogen spin order transfer to produce a hyperpolarized agent may be achieved by double hydrogenation of a substrate or by spin transfer without forming hydrogen bonds. In some aspects, methods for parahydrogen spin order transfer without forming hydrogen bonds includes techniques such as signal amplification by reversible exchange (SABRE). Spin order transfer can be achieved using a dissolved liquid catalyst (known as a homogeneous catalyst) or using a solid catalyst (known as a heterogeneous catalyst) attached to the walls of a fluid channel or within a microreactor. In one non-limiting example, the dissolved liquid catalyst and the solid catalyst comprise a rhodium-based catalyst. RF decoupling or very low magnetic fields induced by shielding may be used to decrease the decay rate of spin order as the volume builds up. Transfer of spin order from protons to the $^{13}C$ or $^{15}N$ nuclei can then be performed with either magnetic field cycling, or radiofrequency (RF) field application. Both of these transfer methods may be implemented as a transient or as a continuous flow process where the time dependence is implemented through spatial dependence of RF and magnetic fields accompanied by a steady velocity of continuous flow.

The spin transfer device 232 may implement small scale spatial field variation with microstrip technology. The spin transfer device 232 may provide further modification to the hydrogenated molecule using methods such as those reported for pyruvate, that is chemical cleaving of an intermediate to provide the final molecule. Using one or more of the methods outlined above, the spin transfer device 232 then outputs the hyperpolarized agent and unreacted reagents to a filtering device 234. The filtering device 234 filters out impurities, catalysts, and unreacted reagents to isolate the hyperpolarized agent. In some aspects, the filtering device 234 includes an ion-exchange filter or other microfluidic separation techniques. The filtering device 234 may use pH and osmolality matching, testing assays, etc. When no cleaving is required, the filtering device 234 may precede the spin transfer device 232.

Figure 3A:
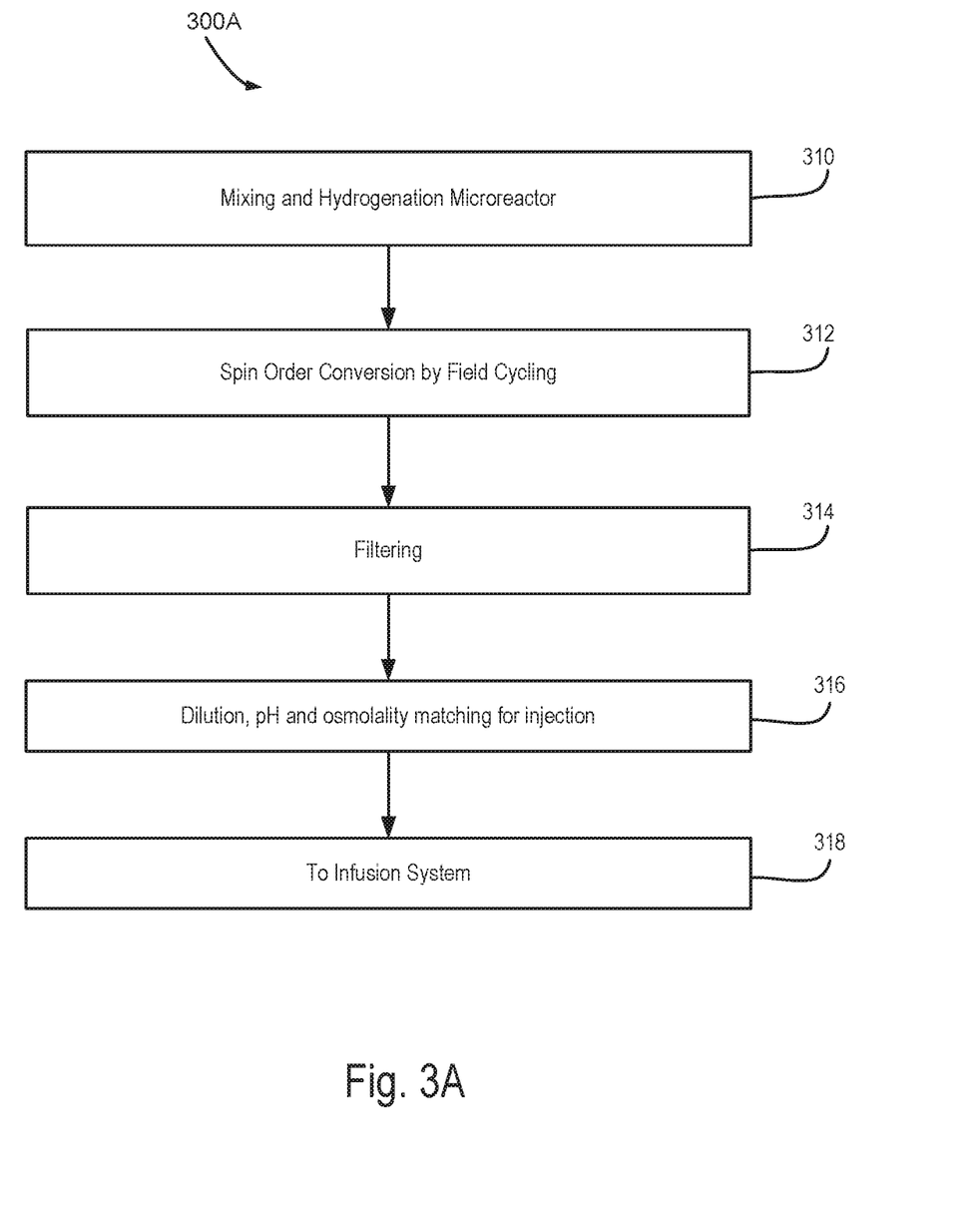
FIG. 3A is an example flow chart setting forth steps of a first method for producing hyperpolarized agents in accordance with the present disclosure.

FIGS. 3A-3D illustrate several examples of flow charts for spin order transfer. FIG. 3A is an example flow chart setting forth steps of a first method 300A for producing hyperpolarized agents in accordance with the present disclosure. The hydrogenation uses an externally supplied homogeneous catalyst. No post hydrogenation chemical alteration of the hyperpolarized agent is required. In step 310, the hyperpolarization and conversion system 230 mixes inputs from the parahydrogen production system 210 and substrate from the substrate production system 220 into a hydrogenation microreactor. The hyperpolarization and conversion system 230 also receives homogeneous catalyst and RF decoupling in step 310. For example, the spin transfer device may receive a homogeneous catalyst from an external supply, such as an external storage vessel. The homogenous catalyst may promote spin order transfer by hydrogenating the substrate with parahydrogen to produce a hyperpolarized agent. In step 312, the hyperpolarization and conversion system 230 may further promote spin order by field cycling. In step 314, the hyperpolarization and conversion system 230 filters out catalyst, impurities, and unreacted reagents to isolate the hyperpolarized agent. In step 316, the hyperpolarization and conversion system 230 dilutes the hyperpolarized agent from step 314 and matches pH and osmolality according to the request, for example, from the MRI system or other system connected to the polarization delivery system. In step 318, the hyperpolarization and conversion system sends the hyperpolarized agent to the infusion system 240.

Figure 3B:
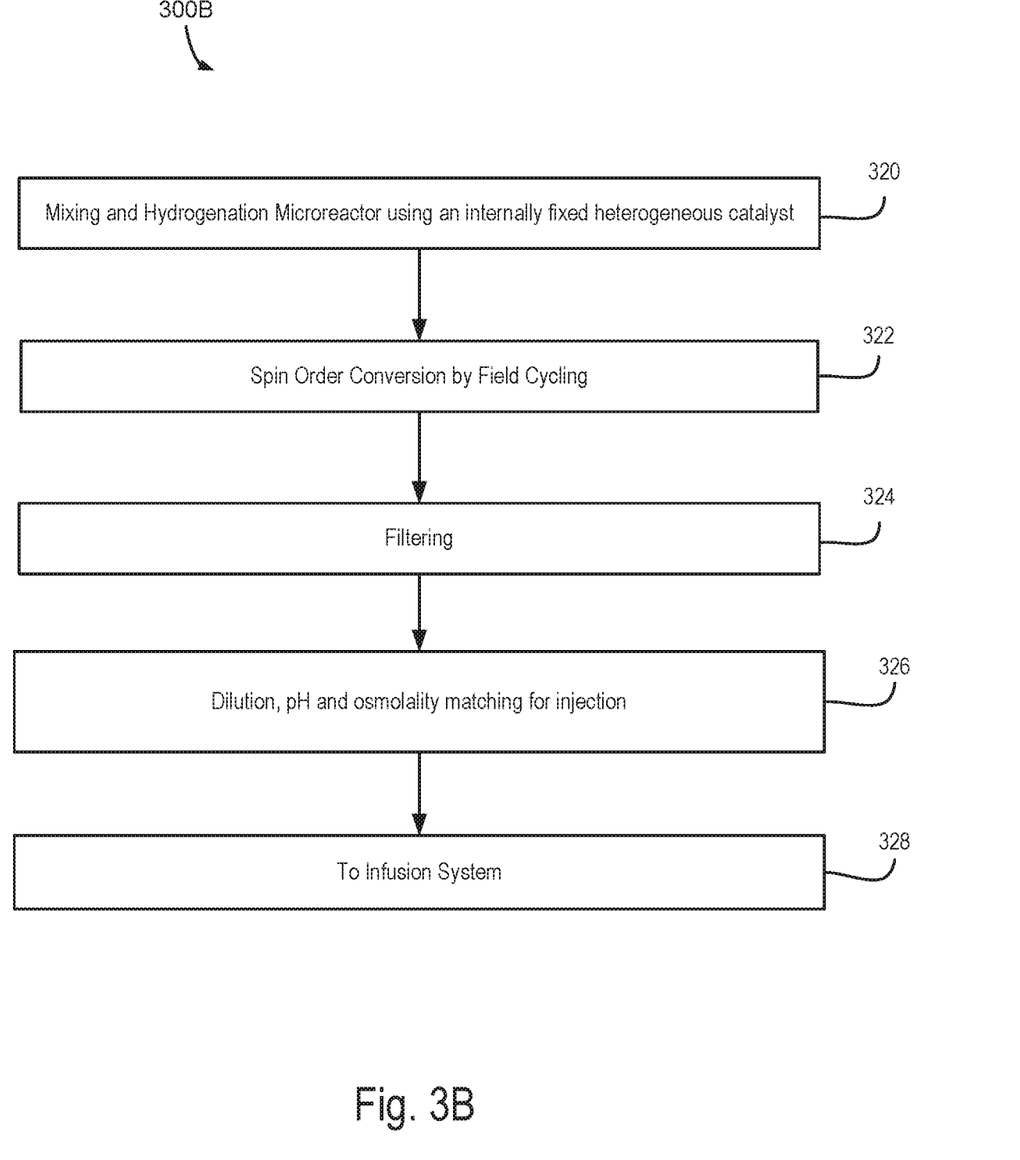
FIG. 3B is an example flow chart setting forth steps of a second method for producing hyperpolarized agents in accordance with the present disclosure.

FIG. 3B is an example flow chart setting forth steps of a second method 300B for producing hyperpolarized agents in accordance with the present disclosure. Here, the hyperpolarization and conversion system 230 achieves hydrogenation using an internally fixed heterogeneous catalyst. Little or no catalyst need be filtered out and no post hydrogenation chemical alteration of the hyperpolarized agent is required using this method. In step 320, the hyperpolarization and conversion system 230 mixes parahydrogen from the parahydrogen production system 210 and substrate from the substrate production system 220 into a hydrogenation microreactor. The heterogeneous catalyst may promote spin order transfer by hydrogenating the substrate with parahydrogen to produce a hyperpolarized agent. The hyperpolarization and conversion system 230 also employs RF decoupling in step 320. In step 322, the hyperpolarization and conversion system 230 converts spin order by field cycling. In step 324, the hyperpolarization and conversion system filters unreacted reagents, impurities, and residual catalyst to isolate the hyperpolarized agent. In step 326, the hyperpolarization and conversion system dilutes the hyperpolarized agent from step 324 and matches pH and osmolality according to the request. In step 328, the hyperpolarization and conversion system sends the hyperpolarized agent to the infusion system 240.

Figure 3C:
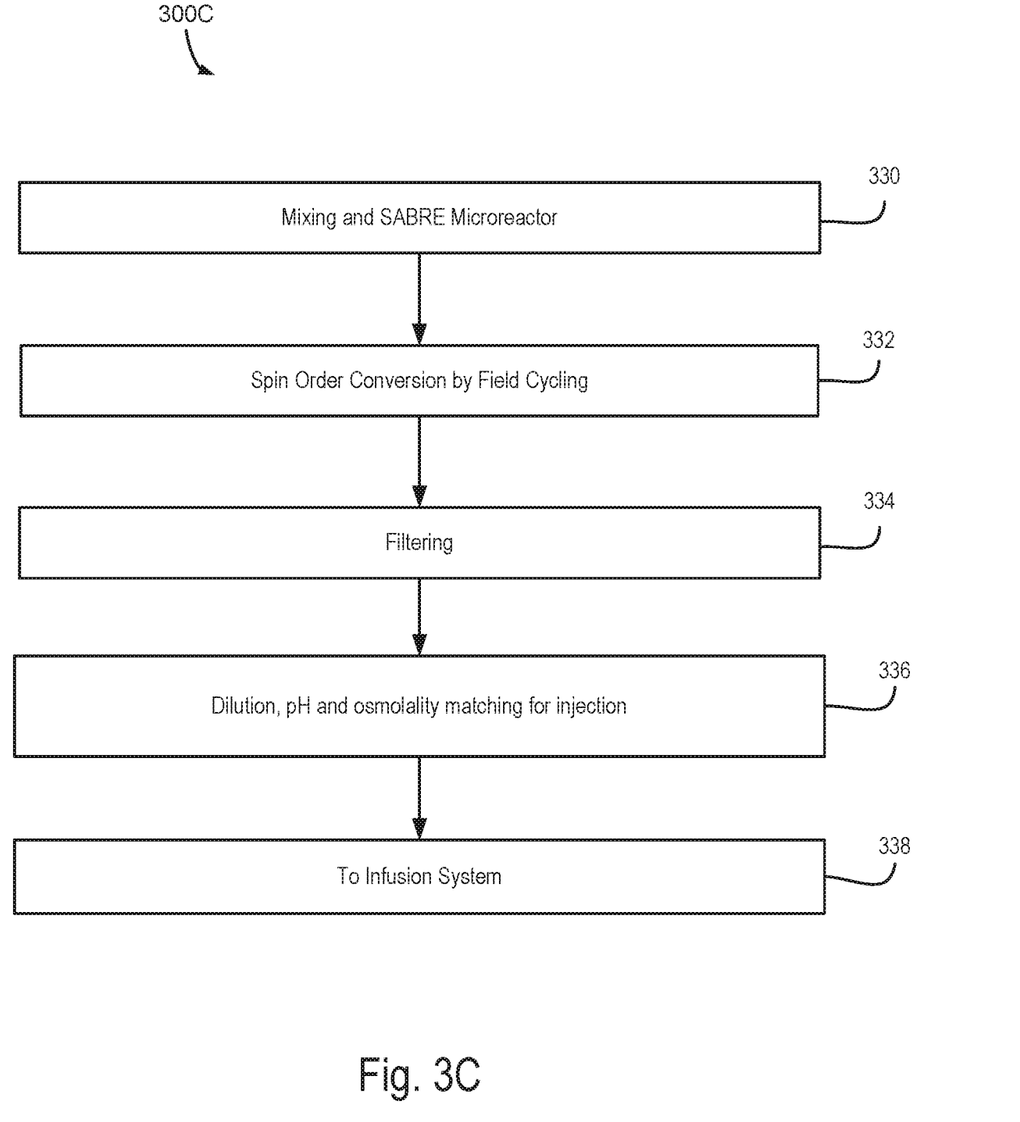
FIG. 3C is an example flow chart setting forth steps of a third method for producing hyperpolarized agents in accordance with the present disclosure.

FIG. 3C is an example flow chart setting forth steps of a third method for producing hyperpolarized agents in accordance with the present disclosure. Here, the hyperpolarization and conversion system employs SABRE using an externally supplied homogeneous catalyst. No filtering out of the substrate or post SABRE chemical alteration of the agent is required. In step 330, the hyperpolarization and conversion system 230 mixes inputs from the parahydrogen production system 210 and substrate from the substrate production system 220 into a SABRE microreactor. Spin order may be transferred from the parahydrogen to the substrate to produce a hyperpolarized agent, where the rate of spin order transfer may be facilitated by the homogenous catalyst. The hyperpolarization and conversion system 230 also employs RF decoupling. In step 332, the hyperpolarization and conversion system 230 converts spin order by field cycling. In step 334, the hyperpolarization and conversion system 230 filters the catalyst, impurities, and unreacted reagents to isolate the hyperpolarized agent. In step 336, the hyperpolarization and conversion system 230 dilutes the hyperpolarized agent from step 334 and matches pH and osmolality according to the request. In step 338, the hyperpolarization and conversion system sends the hyperpolarized agent to the infusion system 240.

Figure 3D:
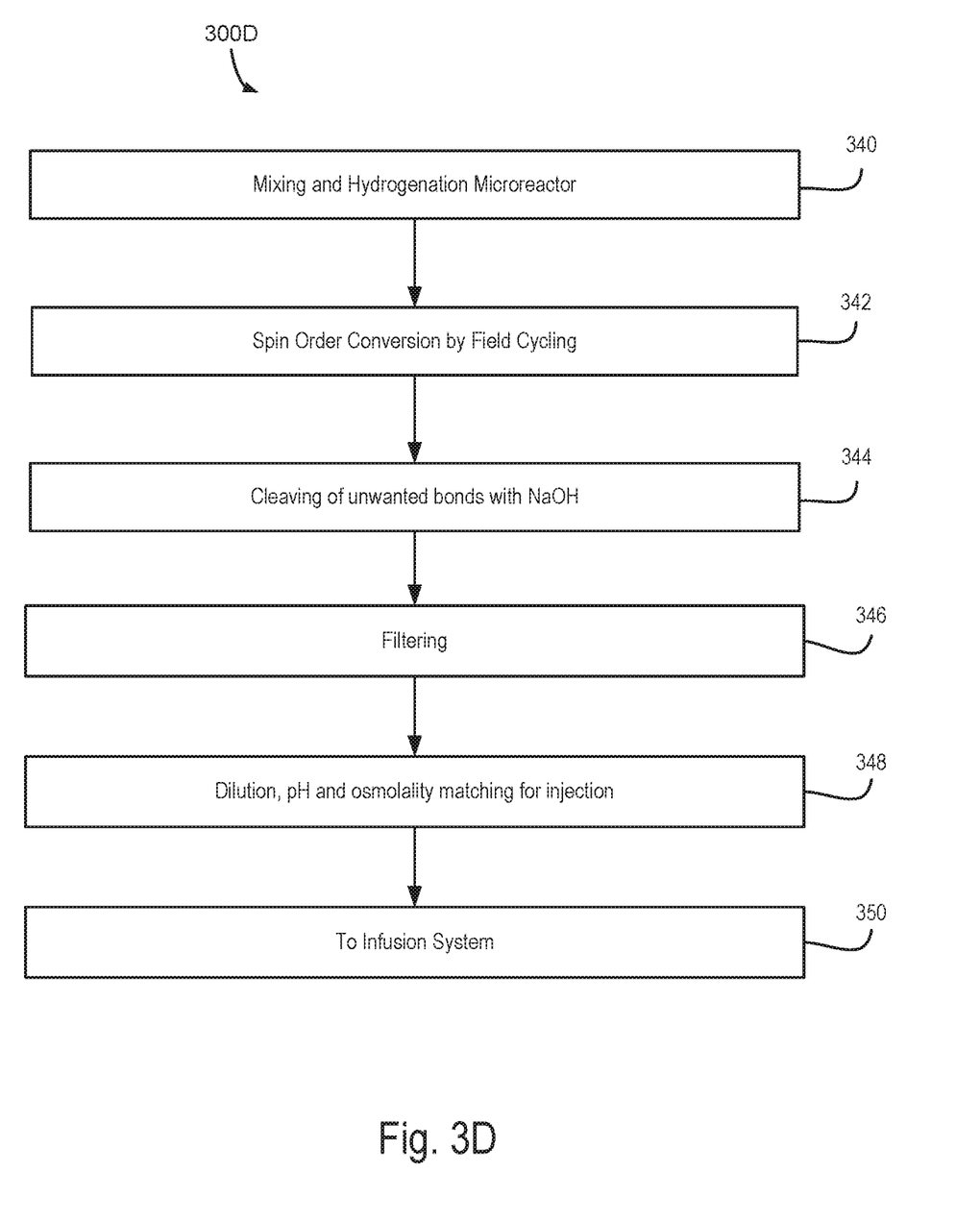
FIG. 3D is an example flow chart setting forth steps of a fourth method for producing hyperpolarized agents in accordance with the present disclosure.

FIG. 3D is an example flow chart setting forth steps of a fourth method for producing hyperpolarized agents in accordance with the present disclosure. Here, the hyperpolarization and conversion system 230 employs hydrogenation using an internally fixed heterogeneous catalyst. Little or no catalyst need be filtered out. Post hydrogenation chemical alteration of the hyperpolarized agent may be required. In step 340, the hyperpolarization and conversion system 230 mixes parahydrogen from the parahydrogen production system 210 and substrate from the substrate production system 220. The hyperpolarization and conversion system 230 also employs RF decoupling. The heterogeneous catalyst may promote spin order transfer by hydrogenating the substrate with the parahydrogen to produce a hyperpolarized agent. In step 342, the hyperpolarization and conversion system 230 converts spin order by field cycling. In step 344, the hyperpolarization and conversion system 230 may cleave unwanted bonds with NaOH. In step 346, the hyperpolarization and conversion system 230 filters unreacted reagents, impurities, and residual catalyst to isolate the hyperpolarized agent. In step 348, the hyperpolarization and conversion system 230 dilutes the hyperpolarized agent and matches pH and osmolality according to the request. In step 350, the hyperpolarization and conversion system 230 sends the hyperpolarized agent to the infusion system 240.

In the above examples, replacement of field cycling with RF pulse methods is feasible. All possible combinations of the basic elements are not shown. RF decoupling may or may not be necessary to lengthen the lifetime of the spin order and could potentially be replaced with performing the operations at very low field. Some of the post-hydrogenation elements, such as spin order conversion, filtering, and dilution may be placed in different orders. The cleaving of unwanted hydrogens, as in FIG. 3D, may need to be performed after spin order conversion.

The disclosed systems and methods for hyperpolarization have greater promise for efficient, safe, inexpensive, and widespread use of hyperpolarized MR tracers. This method is based on PHIP, which is more chemically complex but has shown similar polarization efficiency to DNP. Progress with PHIP has been slow, in part, because of very primitive technology and chemistry sophistication. For example, initially it was felt that metabolic agents of interest, such as pyruvate, could not be polarized by PHIP. Recently however, it was shown that choice of an appropriate substrate and quick chemical modification allows hyperpolarization of pyruvate and potentially many other interesting molecules.

Further, PHIP does not require very low temperatures or high magnetic fields, so miniaturization, cost reduction, and widespread distribution is likely much more feasible than DNP. Still, the field is developing PHIP slowly, with simple batch production methods and without the benefit of state-of-the-art chemical synthesis methods. The hyperpolarized agents may be used as MR tracers for perfusion imaging.

The present disclosure has been described in terms of one or more embodiments, and it should be appreciated that many equivalents, alternatives, variations, and modifications, aside from those expressly stated, are possible and within the scope of the disclosure. For example, it is contemplated that the above-described techniques may be used for on-demand continuous-flow production of polarized substrate for MRI or NMR.

The polarization delivery system may be packaged in a compact, reconfigurable, and mobile system. It is noted that different stages may function more effectively at different temperatures and pressures from each other. For example, hydrogenation may function more effectively at pressures up to 100× atmospheric pressure and at temperatures as low as 0° C. or as high as 100° C. Cooling or heating stages within or between these stages may be necessary to achieve these conditions.

We claim:

1. A polarization delivery system comprising:
a parahydrogen production system comprising a microreactor that processes hydrogen based on a request from a magnetic resonance imaging (MRI) or nuclear magnetic resonance (NMR) system, wherein the microreactor exposes the hydrogen to a catalyst to produce parahydrogen; and
a hyperpolarization and conversion system comprising a spin transfer device that receives the parahydrogen from the microreactor and transfers spin order from the parahydrogen to a substrate, wherein the spin transfer device is a hydrogenation microreactor or signal amplification by reversible exchange (SABRE) microreactor.

2. The polarization delivery system of claim 1 wherein the parahydrogen production system further comprises a micro hydrogen generator.

3. The polarization delivery system of claim 2 wherein the parahydrogen production system further comprises a cooling device connected between the micro hydrogen generator and the microreactor.

4. The polarization delivery system of claim 3 wherein the cooling device comprises a two-stage cooling system using hydrogen as a coolant for a second stage.

5. The polarization delivery system of claim 1, further comprising:
a substrate production system connected to the spin transfer device, the substrate production system comprising a substrate synthesizer that converts input chemicals to the substrate.

6. The method of claim 5, wherein the hyperpolarization and conversion system performs spin order transfer using continuous flow inputs from the substrate production system and the parahydrogen production system.

7. The polarization delivery system of claim 1 wherein the spin transfer device receives a homogeneous catalyst from an external supply.

8. The polarization delivery system of claim 1 wherein the spin transfer device employs a heterogeneous catalyst fixed internally in the spin transfer device.

9. The polarization delivery system of claim 1 wherein the hyperpolarization and conversion system further comprises a filtering device configured to receive polarized substrate from the spin transfer device.

10. The polarization delivery system of claim 9 wherein the filtering device filters out impurities in the polarized substrate and outputs the polarized substrate to the MRI or NMR system.

11. A method for producing polarized hydrogen for use during a magnetic resonance imaging (MRI) or nuclear magnetic resonance (NMR) process, the method comprising:
generating, with a micro hydrogen generator in a polarization delivery system, hydrogen based on a request;
processing, with a microreactor in the polarization delivery system, the hydrogen into parahydrogen based on the request by exposing the hydrogen to a catalyst in the microreactor;
receiving, by a spin transfer device, processed hydrogen from the microreactor; and
transferring, with the spin transfer device, spin order from the processed hydrogen to a substrate, wherein the spin transfer device is a hydrogenation microreactor or signal amplification by reversible exchange (SABRE) microreactor.

12. The method of claim 11 further comprising:
cooling, by a cooling device connected between the micro hydrogen generator and the microreactor, the hydrogen to a first temperature range.

13. The method of claim 11 further comprising:
converting, by a substrate synthesizer connected to the spin transfer device, input chemicals to the substrate.

14. The method of claim 11 further comprising:
receiving, by the spin transfer device, a homogeneous catalyst from an external supply.

15. The method of claim 11 further comprising:
receiving, by a filtering device, polarized substrate from the spin transfer device; and filtering out impurities in the polarized substrate and output the polarized substrate for use in the MRI or NMR process.

16. A method for producing contrast agent, the method comprising:
generating, for use with a magnetic resonance imaging (MRI) or nuclear magnetic resonance (NMR) system performing an MRI or NMR process, a request based on a subject to be scanned in the MRI or NMR system during the MRI or NMR process;
generating, with a micro hydrogen generator in a polarization delivery system, hydrogen based on the request;
processing, with a microreactor in the polarization delivery system, the hydrogen into parahydrogen based on the request by exposing the hydrogen to a catalyst in the microreactor;
receiving, by a spin transfer device, processed hydrogen from the microreactor, wherein the spin transfer device is a hydrogenation microreactor or signal amplification by reversible exchange (SABRE) microreactor; and
transferring, with the spin transfer device, spin order from the processed hydrogen to produce the contrast agent to be injected to the subject.

17. The method of claim 16 further comprising:
receiving, by a filtering device, polarized substrate from the spin transfer device; and
filtering out impurities in the polarized substrate and output the polarized substrate as the contrast agent to be injected to the subject.

18. A microfluidic or microreactor polarization delivery system comprising:
a parahydrogen production system comprising a microfluidic or microreactor that processes hydrogen based on a request from a magnetic resonance imaging (MRI) or nuclear magnetic resonance (NMR) system, wherein the microfluidic or microreactor exposes the hydrogen to a catalyst to produce parahydrogen; and
a hyperpolarization and conversion system comprising a spin transfer device that receives the parahydrogen from the microfluidic or microreactor and transfers spin order from the parahydrogen to a substrate, wherein the spin transfer device is a hydrogenation microreactor or signal amplification by reversible exchange (SABRE) microreactor.

19. The polarization delivery system of claim 18 wherein the parahydrogen production system further comprises a micro hydrogen generator.

20. The polarization delivery system of claim 19 wherein the parahydrogen production system further comprises a cooling device connected between the micro hydrogen generator and the microreactor or microfluidic device.

21. The polarization delivery system of claim 18, further comprising a microreactor or microfluidic substrate production system connected to the spin transfer device, the substrate production system comprising a substrate synthesizer that converts input chemicals into the substrate.

22. The polarization delivery system of claim 18, wherein spin order is transferred to the substrate in a microfluidic or microreactor device.

23. The polarization delivery system of claim 22, wherein the spin order transfer is achieved by at least one of:
hydrogenation of the substrate using a homogeneous catalyst received from an external supply;
hydrogenation of the substrate using a homogeneous or heterogeneous catalyst that is fixed within the spin order transfer device;
reversible exchange to the substrate using a homogeneous catalyst received from an external supply; and
reversible exchange to the substrate using a homogeneous or heterogeneous catalyst that is fixed within the spin order transfer device.

24. The polarization delivery system of claims 22, wherein the spin order transfer device is exposed to a magnetic field to maintain the spin order.

25. The polarization delivery system of claim 18 wherein one or more microfluidic or microreactor devices chemically transform, filter, dilute, or buffer the output of the spin order transfer device.

26. The polarization delivery system of claim 18 further comprising a microfluidic or microreactor device and wherein spin order is converted to magnetization of a non-hydrogen nucleus within the microfluidic or microreactor device by electromagnetic fields modulated by an external device or flow through spatially varying fields.

27. A method for parahydrogen production for imaging comprising:
processing hydrogen using a microfluidic or microreactor based on a request from a magnetic resonance imaging (MRI) or nuclear magnetic resonance (NMR) system, wherein the microreactor exposes the hydrogen to a catalyst to produce parahydrogen; and
receiving the parahydrogen from the microfluidic or microreactor and transferring spin order from the processed hydrogen to a substrate in a spin transfer device, wherein the spin transfer device is a hydrogenation microreactor or signal amplification by reversible exchange (SABRE) microreactor.

28. The method of claim 27 further comprising at least one of exposing the hydrogen to high surface area catalysts and warming the hydrogen to a preset temperature for subsequent reactions.

29. The method of claim 27 further comprising using a substrate synthesizer to convert input chemicals into the substrate.

30. The method of claim 27 wherein transferring the spin order includes performing hydrogenation of the substrate using at least one of a homogeneous catalyst received from an external supply or a homogeneous or heterogeneous catalyst.

31. The method of claim 27 wherein transferring the spin order includes performing a reversible exchange to the substrate using at least one of a homogeneous catalyst received from an external supply or a homogeneous or heterogeneous catalyst.

32. The method of claims 27 further comprising using a magnetic field to maintain the spin order.

* * * * *

UNITED STATES PATENT AND TRADEMARK OFFICE
CERTIFICATE OF CORRECTION

PATENT NO. : 11,366,186 B2
APPLICATION NO. : 16/323596
DATED : June 21, 2022
INVENTOR(S) : David Alsop et al.

It is certified that error appears in the above-identified patent and that said Letters Patent is hereby corrected as shown below:

In the Specification

Column 1, Line 19, "(MM)" should be --(MRI)--.

Column 1, Line 36, "Bo" should be --$B_0$--.

Signed and Sealed this
Eighth Day of November, 2022

Katherine Kelly Vidal
*Director of the United States Patent and Trademark Office*